(12) United States Patent
Paige

(10) Patent No.: US 8,201,454 B2
(45) Date of Patent: Jun. 19, 2012

(54) PIPELINE INSPECTION APPARATUS AND METHOD

(75) Inventor: David Paige, Newcastle upon Tyne (GB)

(73) Assignee: PII Limited, Cramington (GB)

( * ) Notice: Subject to any disclaimer, the term of this patent is extended or adjusted under 35 U.S.C. 154(b) by 478 days.

(21) Appl. No.: 12/438,900

(22) PCT Filed: Nov. 5, 2008

(86) PCT No.: PCT/GB2008/003725
§ 371 (c)(1),
(2), (4) Date: Feb. 25, 2009

(87) PCT Pub. No.: WO2009/087342
PCT Pub. Date: Jul. 16, 2009

(65) Prior Publication Data
US 2011/0041612 A1    Feb. 24, 2011

Related U.S. Application Data

(60) Provisional application No. 61/020,648, filed on Jan. 11, 2008.

(51) Int. Cl.
*A61B 5/04* (2006.01)
*G01N 29/04* (2006.01)

(52) U.S. Cl. ......................................... 73/623
(58) Field of Classification Search .............. 73/623
See application file for complete search history.

(56) References Cited

U.S. PATENT DOCUMENTS

| | | | |
|---|---|---|---|
| 4,375,165 A | 3/1983 | De Sterke | |
| 5,907,100 A * | 5/1999 | Cook | 73/602 |
| 6,848,313 B2 * | 2/2005 | Krieg et al. | 73/628 |
| 7,299,697 B2 * | 11/2007 | Siddu et al. | 73/597 |
| 2007/0211572 A1* | 9/2007 | Reiderman et al. | 367/35 |

FOREIGN PATENT DOCUMENTS

| | | |
|---|---|---|
| DE | 3309470 A1 | 9/1984 |
| EP | 0775910 A | 5/1997 |
| EP | 1333277 A2 | 8/2003 |
| WO | 03/021249 A | 3/2003 |
| WO | 2005045418 A | 5/2005 |

OTHER PUBLICATIONS

New Pig for Gas Pipeline Crack Inspections—Enhancements Derived from 5 Years' Operational Experience, David Allen et al., Jan. 6, 2009 (also presented at the 3$^{rd}$ Pipeline Technology Conference 2008, Apr. 23, 2008, Session 4—see attached conference flyer).

(Continued)

*Primary Examiner* — Lisa Caputo
*Assistant Examiner* — Jamel Williams
(74) *Attorney, Agent, or Firm* — GE Global Patent Operation

(57) ABSTRACT

Ultrasonic pipeline inspection apparatus which utilizes two different wave modes (e.g. a horizontally polarized shear mode and a symmetric Lamb wave mode) to discriminate different defect types by comparing corresponding signals collected from defects. EMATs may detect the signals. The detected amplitudes of the collected signals from both wave modes are compared to calculate a ratio, which may be compared with a distribution of ratio values for known defects to evaluate the type of defect detected. The apparatus may be a sensor module mountable on a pipeline vehicle and having a plurality of sensors distributed around its periphery.

11 Claims, 2 Drawing Sheets

OTHER PUBLICATIONS

Improvements in Pigging Technology Presentation—New Pig for Gas Pipeline Crack Inspections—Enhancements Derived from 5 years' Operational Experience (presented at the 17$^{th}$ Colloquium, Prague Safety and Reliability of Pipelines, May 12$^{th}$ and 13$^{th}$, Presenter: Jurgen Ehnrhardt—see attached conference flyer).

Improvements in Pigging Technology Presentation—Metal Loss—"Unpiggable" Pipelines (presented at the 17$^{th}$ Colloquium, Prague Safety and Reliability of Pipelines, May 12$^{th}$ and 13$^{th}$, Presenter: Jurgen Ehnrhardt—see attached conference flyer).

Werner Bahr: "EMAT-Molch. Sicherung der Integritt:it von GasPipelines" [Online] Jan. 12, 2005, XP002514155.

PCT Search Report and Written Opinion issued Feb. 18, 2009 in connection with Application No. PCT/GB2008/003725.

Werner Bahr: "EMAT-Molch, Sicherung der Integritt:it von GasPipelines",[Online] Jan. 12, 2005, XP002514155.

EP Office Action issued in corresponding EP Application No. 08 870 405,1-1240, dated May 27, 2011.

\* cited by examiner

PIPELINE INSPECTION APPARATUS AND METHOD

TECHNICAL FIELD

The invention relates to apparatus for and methods of inspecting the integrity of pipelines. For example, it may relate to the internal inspection of operational pipelines using pipeline vehicles.

BACKGROUND TO THE INVENTION

To maintain the integrity of pipelines, it is known to employ inspection vehicles that travel internally to the pipe recording information about the quality of the pipe wall. The majority of these inspection vehicles use ultrasonic or magnetic sensors to carry out the inspection.

The preferred technology for crack detection is ultrasonic inspection, and in pipelines carrying liquids a vehicle-based inspection system can use the liquid as a coupling medium to assist conventional piezo-electric sensors. These sensors are capable of carrying out well-established inspection techniques leading to high resolution of defects and discrimination of defects based on through-wall positional resolution. In gas filled pipelines it is difficult to use conventional piezo-electric transducers because the gaseous pipeline product is not an efficient coupling medium for introducing ultrasound into the pipe wall.

An alternative type of sensor, which does not rely on liquid coupling, is an electromagnetic acoustic transducer (EMAT).

EMATs are dry-coupled. They generate sound directly in the test material by one of two main mechanisms. A first mechanism involves Lorentz forces, a second mechanism involves magnetostrictive forces. For transmission into the pipe wall according to the first mechanism, an alternating current in a wire induces an eddy current in the metal surface. When this is combined with a static magnetic field, a Lorentz force may be produced that causes the "grid" of metal in the pipe wall to oscillate, launching ultrasonic sound waves in the pipe wall. Breaks in the homogeneity of this metal grid (e.g. defects such as cracks) will result in reflections of the sound wave. These reflected waves encountering the magnetic field will generate an eddy current, which in turn, induces a current in the wire. This current forms the received signal, which can be further processed and analyzed. EMATs transmitting according to the second mechanism rely on magnetostrictive forces that result from the AC magnetic field. These EMATs may receive sound an convert it to an electrical signal by the inverse magnetostrictive effect.

EMATs can be used to perform ultrasonic inspection of gas pipelines. However, the spatial resolution of the inspection is usually lower than for conventional (e.g. piezo-electric) sensors operating in pipelines which carry liquid. A consequence of this is that EMAT sensors, which are able to detect reliably the presence of pipe wall defects, are comparatively poor at providing sufficient information to identify the type of pipe wall defect.

SUMMARY OF THE INVENTION

At its most general, the invention proposes the use of two different wave modes in ultrasonic pipeline inspection, wherein a comparison of the corresponding signals collected from a defect is indicative of the nature of the defect. The invention may thus provide a means of discriminating between crack defects and other feature types in the wall of a pipeline, e.g. lamination and inclusion features, while carrying out ultrasonic testing.

According to the invention there may be provided pipeline inspection apparatus including a first ultrasound sensor for generating in a pipe wall a first ultrasonic guided wave having a first mode, a second ultrasound sensor for generating in the pipe wall a second ultrasonic guided wave having a second mode different from the first mode, and a detector for collecting respective responses to the first and second ultrasonic guided waves. The detector may detect the amplitudes of the collected signals from both wave modes e.g. to permit a subsequent comparison to be performed to determine the type of defect present in an inspected pipeline. The comparison may include calculating a ratio of the amplitudes. The calculated ratio may be compared to a distribution of ratio values for known defects to evaluate the type of defect detected.

The defects that may be determined and hence distinguished by the invention can include crack-like defects (e.g. cracks or other formations which result in separation of material along planes that are substantially perpendicular to the pipe wall), inclusion-like defects (e.g. lamination at junctions between layers of pipe wall material or inclusions), notch-like defects (e.g. scratches or other formations resulting from material being scraped or otherwise removed from a pipe wall surface), and geometry-related (e.g. caused by longitudinal weld beads or the like). The invention may permit a distinction to be drawn between injurious defects, such as cracks, and non-injurious defects, such as laminations.

The first and second ultrasound sensors may each be an electromagnetic acoustic transducer (EMAT). Each sensor may also be the detector for echo signals corresponding to its respective wave mode. The sensors may be arranged to transmit their guided waves towards a common region, i.e. so that an inspection location on a pipeline wall may be exposed to both wave modes. Each sensor may comprise a mode generator adapted to generate its respective mode. The mode generator may include an excitation winding arranged to excite the respective wave mode in a particular direction. The sensors are preferably arranged to direct the wave modes in a common direction. EMAT sensors operate using an external magnetic field. The first and second sensors may use the same magnetic field. For example, the mode generator for each wave mode may be contained in the same housing. An external magnetic field may be effective in the housing to permit operation of the sensors.

As mentioned above, EMATs may be used to perform ultrasonic inspection of gas pipelines, i.e. no liquid medium is required to couple ultrasonic waves to and from the pipe wall. The dual wave mode idea of the invention provides an advantage over conventional EMAT arrangements because it is able to distinguish between the defects that cannot be spatially resolved.

The first and second wave modes may be orthogonal to each other. For example, the first wave mode may include a horizontally polarised shear (SH) mode and the second wave mode may include a symmetric Lamb wave mode, e.g. the fundamental symmetric mode S0. This combination of modes is particularly useful when inspecting commercial steel pipelines because the distributions of ratios for different types of defect have little overlap, which facilitates classification (discrimination) of different defect types.

Both the symmetric Lamb wave mode and the shear wave mode may have a wavelength similar to the pipe wall thickness. Waves having these wavelengths are long enough to propagate unattenuated over large sectors of steel pipeline but short enough to allow useful circumferential and axial position resolution needed for comparison between the two mode types. In addition, the horizontally polarised shear mode may have a wavelength arranged to permit efficient generation of the fundamental wave mode and at least one higher shear wave mode. The higher shear wave mode may provide further options for comparing the responses of the different modes to the defect. This may increase discrimination accuracy.

In use the wave modes may be excited in the pipe wall in a manner to reduce or minimise interference or cross-talk. Each mode may be transmitted at separate times, or may be transmitted simultaneously from sensors which are physically displaced to avoid significant interference.

In one embodiment the apparatus may comprise a sensor module mountable on a pipeline vehicle. The sensor module may have a plurality of SH and S0EMAT sensors distributed around its periphery so as to achieve full inspection coverage of the pipeline wall with SH and S0 waves as the vehicle travels within the pipeline.

The sensor module may have one or more pairs of each EMAT sensor type, the members of each pair being separated from each other around the pipeline vehicle circumference. The separation is arranged so that the members of each pair may lie on opposite sides of a defect. In this embodiment signals of each wave mode transmitted past the defect may be obtained in addition to echo signals from the defect itself to improve the accuracy of the comparison between echo signals of each wave mode. For example, the detected transmitted signals may be used to compensate for variations in wall thickness and the like, which may affect each wave mode differently.

Thus, each pair of sensors may be configured to transmit signals therebetween to allow regular calibration of the sensor performance throughout the inspection record and facilitate the comparison of signal amplitudes that permits defect discrimination.

In addition, the drop in signal due to the intervention of a defect between a pair of sensors can be used to form alternative mode ratios. These ratios are thus based on signals transmitted between sensors rather than on echo signals.

BRIEF DESCRIPTION OF THE DRAWINGS

An embodiment of the invention is described below with reference to the accompanying drawings, in which.

DETAILED DESCRIPTION

Further Options and Preferences

Figure 1:
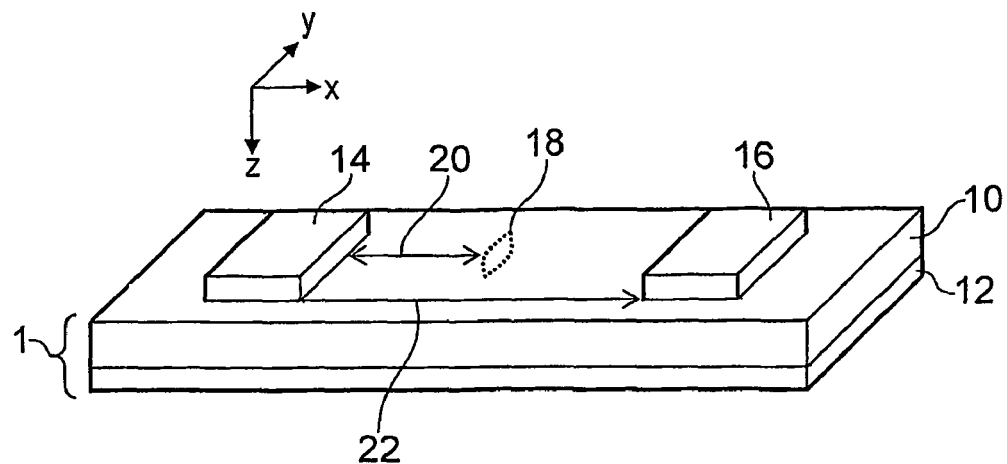
FIG. 1 is a perspective view of a section of pipe wall to illustrate the theory behind the invention.

FIG. 1 is a schematic diagram of a pipe wall 1 that is useful to illustrate the principles of the invention. The pipe wall 1 comprises a metal e.g. steel layer 10 which has a protective outer coating 12 e.g. or bitumen or a polymer material bounded to it. In FIG. 1 the pipe wall is shown to be flat. In reality it is curved e.g. to form a tube with an axis extending in either the x or the y direction.

The inspection apparatus of the invention may have two sensors 14, 16 arranged to contact the inner surface of the metal layer 10 at circumferentially spaced locations (i.e. locations separately in the x direction). Each of the sensors 14, 16 may be positioned at a distance from a defect 18 to be tested. The sensors 14, 16 are EMATs arranged to generate guided acoustic (ultrasonic) waves in the metal layer 10. To enable the type of defect to be determined, the sensors 14, 16 are arranged to generate two different types of acoustic wave. This may be achieved by providing separate generating means for each of the wave types in each of the sensors 14, 16, or having a separate pair of sensors for each wave type wherein the second pair of sensors may be moved into positions or activated after the first pair have performed their inspection. An example of the different wave types that can be used is the horizontally polarized (i.e. main particle motion in the y direction) shear wave mode (SH) and the fundamental mode of a symmetric Lamb wave (S0). The sensors 14, 16 are arranged such that the propagation of the guided waves is substantially in the direction perpendicular to the direction of defect types (e.g. cracks, etc.) that are of interest for inspection purposes.

As illustrated in FIG. 1, first sensor 14 is performing a transmitting and receiving function whilst second sensor 16 is performing only a receiving function. The sensors 14, 16 may additionally operate the other way round to obtain additional information and hence improve the inspection accuracy of the apparatus.

First sensor 14 thus generates a guided wave in the metal layer 10. Part of the guided wave reflects off the defect 18. This reflected wave 20 is received by the first sensor 14 (i.e. causes an echo signal to be generated in the EMAT), where it is measured. Where EMATs are used, the amplitude and other characteristics, e.g. frequency, of the echo signal may be measured. Part of the generated guided wave may travel past or be transmitted by the defect 18. This transmitted wave 22 is received by the second sensor 16 and measured in a corresponding manner to the reflected wave 20.

This measurement may be used to compensate the reflected wave measurement for variation in pipe properties, as discussed in detail below. The change in signal may also be used as an indicator for the defect, e.g. used directly to evaluate the defect type. The above measurement process is then repeated for the other wave type. The measured signals for each wave type may then be compared (after appropriate compensation and calibration) to provide information about the defect 18 (e.g. the defect type). One example of a suitable comparison parameter is the ratio between echo signal amplitudes for the two wave types e.g. as detected by their respective EMATs.

Figure 2:
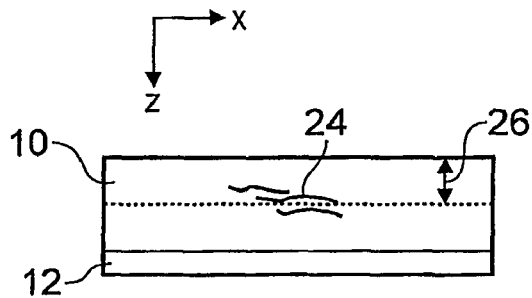
FIG. 2 is a cross-section of a pipe wall having inclusion-type features.
Figure 3:
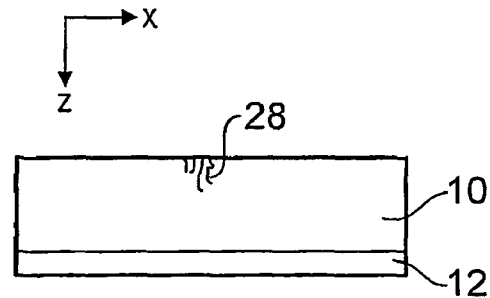
FIG. 3 is a cross-section of a pipe wall having crack-type features.

FIGS. 2 and 3 show two different types of defect that can be distinguished using the technique described above even though the spatial resolution of the EMATs is limited, i.e. not good enough to provide through wall position information about the defect. For example, FIG. 2 illustrates inclusion-like defects 24 in the metal layer 10. The technique of the invention can identify them as such even though the EMATs may not be able to provide information about the through wall position 26 of those defects. FIG. 3 illustrates crack-like defects 28 at the inner surface of the metal layer 10. These defects are potentially injurious, whereas the defects 24 shown in FIG. 2 may be benign. The invention permits the defects 24, 28 to be distinguished in an accurate and repeatable manner.

Figure 4:
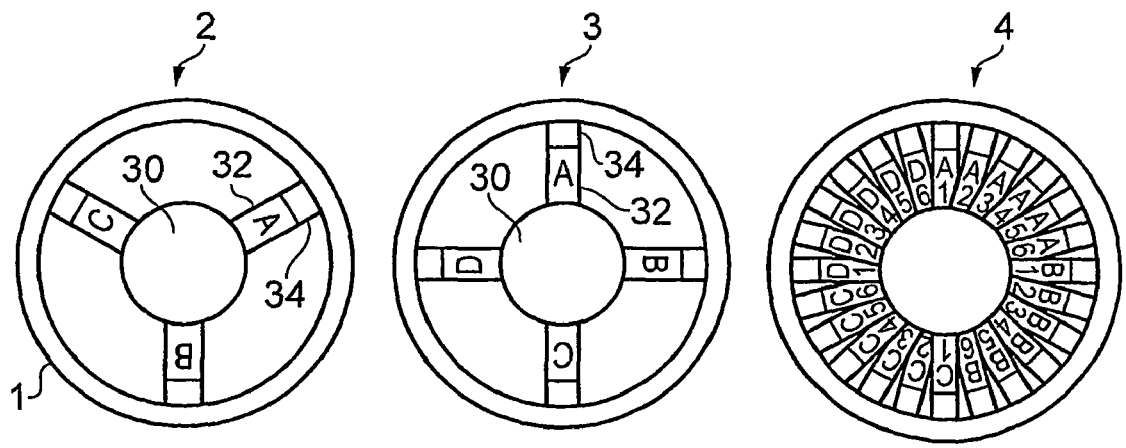
FIG. 4 is a front view of a plurality of sensor carriers that can be used in an embodiment of the invention.

In a practical embodiment, the sensors are mounted on a sensor module which may be carried by a pipeline inspection vehicle arrived to travel along the interior of a pipe. The sensors are desirably located as close to the inner surface of the pipe as possible to maximise the efficiency of energy transfer from the sensor into the pipe. Accordingly, the sensor module may comprise one or more sensor carriers, each sensor carrier comprising a central hub arranged to support one or more sensors around its periphery. The hub may have a number of arms projecting radially therefrom. Each arm may support a sensor. FIG. 4 depicts two types of sensor carrier. A three-armed sensor carrier 2 has a central hub 30 with three radially extending arms 32 located at equal angular spacing therearound. A sensor 34 e.g. an EMAT is mounted at the end of each arm 32. The sensor 34 may include a mode generator for two different wave modes. A four-armed sensor carrier 3 is arranged in a similar manner, with four arms 32 arranged at 90° intervals therearound and sensors 34 at the end of each arm 32. The sensors 34 are arranged to contact the pipe wall 1. A protective (i.e. wear resistant) layer (not shown) may be provided on each sensor at the contact interface with the inner pipe surface.

FIG. 4 also shows a sensor module 4 that comprises a plurality (six in this example) of axially adjacent four-armed sensor carriers. Each sensor carrier has a small angular displacement from its neighbour whereby substantially all of the pipe interior surface is covered by a sensor. Each arm on the sensor carrier has its own sensor, which is arranged to form a pair with each of the other sensors to collect data. In this embodiment each carrier operates essentially independently (i.e. sensors on different carrier do not communicate with each other). However, in principle it may be possible for sensors on one carrier to communicate with sensors on another carrier, e.g. to provide addition data about detected defects.

The sensors are positioned to maximise signal to noise ratio (SNR). In this contact, a signal for each sensor may comprise a guided wave from an adjacent sensor (to provide e.g. information about the pipe wall in that region) or a guided wave from the sensor itself that is reflected from a defect. Noise may come from the guided waves of other sensors that are transmitted through the pipe or scattered by defects. The guided waves are attenuated as they travel in the pipe wall because of the protective coating bounded thereto. Signal strength is therefore improved by providing the sensors close to one another. However, this can also increase noise. The four-armed sensor carrier 3 depicted in FIG. 4 is an optimised solution for a pipe with a diameter of 24-30 inches (61-76 cm).

The present invention is based on the premise that the two (or more) guided wave types are affected by different defect types in distinct ways. For example, defect type A may reflect 50% of an incident SH1 wave and 20% of an S0 Lamb wave, whereas defect type B may reflect 40% of an incident SH1 wave and 50% of an S0 Lamb wave. In this case a ratio of the reflected portions, i.e. 50/20 compared with 40/50, may yield a parameter that enables the defect types to be distinguished. In practice, the ratios are likely to form a distribution for each defect type. If the distributions can be resolved (are sufficiently spaced), the defects may be distinguished.

To obtain an accurate measurement of the parameter, it may be necessary to compensate for other factors which affect the reflected signal and/or to calibrate the signal to account for variations (e.g. systematic errors) between different sensors. For example, the following factors may affect the guided wave energy that (i) reaches a defect from a sensor, and (ii) is reflected or transmitted to the same or another sensor:

(a) transmitter efficiency, which may be affected by the fundamental (base line) efficiency of the sensor, variations or drift in the amplifying or receiving components, and thickness of the protective surface (wear plate) in contact with the pipe wall;

(b) electromagnetic radiation coupling efficiency between the sensor and pipe wall, which may be affected by debris on the inner surface or space between the sensor and surface e.g. when the sensor bumps over a weld; and (c) signal attenuation in the pipe wall, which may be affected by the pipe wall thickness, the outer coating bounded to the metal layer, natural divergence of the guided wave, and scattering effects.

Some of these factors are related to the measuring apparatus and therefore may be addressed by calibration. Others are local effects caused by conditions around the defect and may be compensated by taking further measurements. For example, a direct transmission signal between closely adjacent sensors may be relatively unaffected by attenuation of sound in the pipe, whereas signals between more distant sensors may be significantly affected. This means that a comparison of signals received over different direct transmission paths can yield information about other factors which may be causing changes in a reflected signal.

Figure 5:
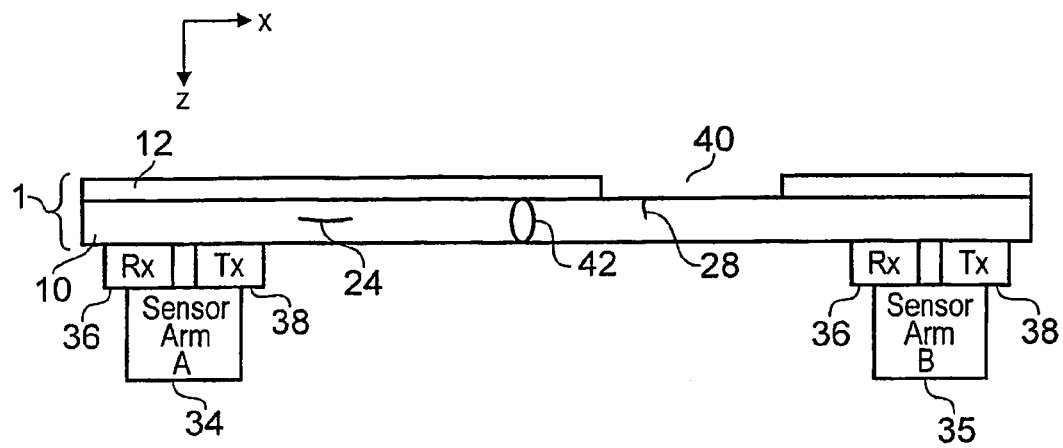
FIG. 5 is a cross-section of a pipe wall with a pipeline inspection apparatus according to one embodiment of the invention in an inspection position.

FIG. 5 illustrates schematically some of the factors that can affect signal attenuation. The pipe wall 1 has a metal layer 10 and an outer protective coating 12 as described above. Two adjacent sensors 34, 35 contact the inner surface of the pipe wall. Each sensor has a receiving section 36 and a transmitting section 38. Also illustrated are features that would affect a signal travelling between the sensors. An inclusion-type defect 24 and a crack-type defect 28 have been discussed above with respect to FIGS. 2 and 3. FIG. 5 also shows a disbond portion 40 where the outer coating 12 is detached from the metal layer 10. This may affect the attenuation of a signal, i.e. the path of a reflected signal to crack 28 from sensor 35 may pass under a larger disbond portion than the path of a reflected signal from sensor 34. A seam weld 42 may also cause additional scattering.

Compensation of signal for local attenuation effects may be achieved by the provision of a pair of each sensor type in a fixed spatial relation on the sensor carrier (inspection vehicle). By measuring the amplitude and arrival times of signals transmitted between the pair of sensors, a relationship for attenuation may be obtained and applied to the reflected signal. For example, attenuation may be dominated by effects due to wall thickness and disbondment of the outer coating. At least two different transmission signals (e.g. between different sensor pairs on a sensor carrier) may provide the necessary data to enable effective compensation of the reflected signals to be carried out. If a more detailed attenuation map may be obtained by comparing transmission signal amplitudes between each pair of a plurality or all sensors on a vehicle. An additional benefit of such an attenuation map is that it may provide an indication of area where the bond integrity between the outer coating and metal layer is different.

Disbondments (failure in bonding between the outer coating and metal layer) may be an early warning of stress corrosion cracking (SCC), which is a major threat to pipeline integrity. The attenuation map may permit preventative action to be taken before SCC actually occurs.

Calibration of sensor efficiencies enables the two types of signal to be consistently compared, irrespective of the sensors used to generate and measure those signals. This may be achieved by comparing the received signal with a known response for that sensor for a standard reflector, e.g. a through wall slot. Alternatively, if a plurality of sensor of the same type are mounted on an inspection vehicle calibration may be achieved by obtaining (in advance) a measurement of the relative efficiencies of the sensors e.g. with respect to a selected "reference" sensor. Calibration can be carried out on each sensor type to obtain relative sensor efficiencies for transmitting and receiving as described below.

Referring to the four-armed sensor carrier 3 in FIG. 4, base line efficiencies for the sensors A, B, C, D may be calculated by collecting data in a commissioning tube. Data would need to be collected from a number of different transmission signals, i.e. 90°, 180° and 0° (if available). A method for doing this is explained in more detail below.

The baseline efficiency of each sensor can be determined from the set of equations below, in which $X_\alpha(T_\beta R_\gamma)$ is the value of a signal from transmitter β that is received by receiver γ, which are separated by angle α, $E_{T\beta}$ is the efficiency of transmitter β, $E_{R\gamma}$ is the efficiency of receiver γ, and TL(α) is the transmission loss factor, sometimes called attenuation, associated with the path length around α degrees of the pipe wall, with the +/− indicating if it is the long or short path between transmitter/receiver pairing. These equations are derived from the transmissions signals on a single sensor carrier for one sensor type. It should be noted that the first term is a value measured on the tool.

$$X_0(T_A R_A) = E_{TA} \cdot E_{RA} \cdot TL(0)$$

$$X_0(T_B R_B) = E_{TB} \cdot E_{RB} \cdot TL(0)$$

$$X_0(T_C R_C) = E_{TC} \cdot E_{RC} \cdot TL(0)$$

$$X_0(T_D R_D) = E_{TD} \cdot E_{RD} \cdot TL(0)$$

$$X_{90}(T_A R_B) = E_{TA} \cdot E_{RB} \cdot TL(90-)$$

$$X_{90}(T_B R_A) = E_{TB} \cdot E_{RA} \cdot TL(90+)$$

$$X_{90}(T_D R_A) = E_{TD} \cdot E_{RA} \cdot TL(90-)$$

$$X_{90}(T_A R_D) = E_{TA} \cdot E_{RD} \cdot TL(90+)$$

$$X_{90}(T_B R_C) = E_{TB} \cdot E_{RC} \cdot TL(90-)$$

$$X_{90}(T_C R_B) = E_{TC} \cdot E_{RB} \cdot TL(90+)$$

$$X_{90}(T_C R_D) = E_{TC} \cdot E_{RD} \cdot TL(90-)$$

$$X_{90}(T_D R_C) = E_{TD} \cdot E_{RC} \cdot TL(90+)$$

$$X_{180}(T_A R_C) = E_{TA} \cdot E_{RC} \cdot TL(180-)$$

$$X_{180}(T_A R_C) = E_{TA} \cdot E_{RC} \cdot TL(180+)$$

$$X_{180}(T_C R_A) = E_{TC} \cdot E_{RA} \cdot TL(180-)$$

$$X_{180}(T_C R_A) = E_{TC} \cdot E_{RA} \cdot TL(180+)$$

$$X_{180}(T_B R_D) = E_{TB} \cdot E_{RD} \cdot TL(180-)$$

$$X_{180}(T_B R_D) = E_{TB} \cdot E_{RD} \cdot TL(180+)$$

$$X_{180}(T_D R_B) = E_{TD} \cdot E_{RB} \cdot TL(180-)$$

$$X_{180}(T_D R_B) = E_{TD} \cdot E_{RB} \cdot TL(180+)$$

The set of equations may differ depending on the sensor type. In the above example there are 20 equations, the number of variables is 8 sensor efficiencies, 4 direct transmission losses and 16 other transmission losses paths. Even if the efficiency of one transmitter and one receiver is set to a reference value it is not possible to solve the set of equations. They can be solved, however, if the attenuation is considered to be uniform around the circumference of the commissioning tube. This may be ensured by using a pipe that is uncoated (or has just a thin coat of paint) and by grinding the seam weld flat. Uniformity of attenuation may be verified by independent experimental measurements. When this is established, it is possible to solve the set of equations to determine the efficiency product of any arbitrary transmitter/receiver pair of without using the direct transmission signals or having to set reference sensors.

Using this arrangement it will be also possible to correlate the efficiencies of sensors on different sensor carriers.

An example of how this may be done is shown below for the case where the direct transmission signal has been difficult to measure. The table below shows the values obtained during the commissioning. The attenuation may be derived from the path length and the knowledge that it is 10 dB/m in this particular example.

|  | Path length (m) | Attenuation (dB) | Signal (dB) |
|---|---|---|---|
| $X_0(T_A R_A) = E_{TA} \cdot E_{RA} \cdot TL(0)$ | 0 | — | Not measured |
| $X_0(T_B R_B) = E_{TB} \cdot E_{RB} \cdot TL(0)$ | 0 | — | Not measured |
| $X_0(T_C R_C) = E_{TC} \cdot E_{RC} \cdot TL(0)$ | 0 | — | Not measured |
| $X_0(T_D R_D) = E_{TD} \cdot E_{RD} \cdot TL(0)$ | 0 | — | Not measured |
| $X_{90}(T_A R_B) = E_{TA} \cdot E_{RB} \cdot TL(90-)$ | 0.4 | 4.0 | 66.5 |
| $X_{90}(T_B R_A) = E_{TB} \cdot E_{RA} \cdot TL(90+)$ | 0.6 | 6.0 | 65.0 |
| $X_{90}(T_D R_A) = E_{TD} \cdot E_{RA} \cdot TL(90-)$ | 0.4 | 4.0 | 61.0 |
| $X_{90}(T_A R_D) = E_{TA} \cdot E_{RD} \cdot TL(90+)$ | 0.6 | 6.0 | 62.5 |
| $X_{90}(T_B R_C) = E_{TB} \cdot E_{RC} \cdot TL(90-)$ | 0.4 | 4.0 | 66.0 |
| $X_{90}(T_C R_B) = E_{TC} \cdot E_{RB} \cdot TL(90+)$ | 0.6 | 6.0 | 65.0 |
| $X_{90}(T_C R_D) = E_{TC} \cdot E_{RD} \cdot TL(90-)$ | 0.4 | 4.0 | 65.0 |
| $X_{90}(T_D R_C) = E_{TD} \cdot E_{RC} \cdot TL(90+)$ | 0.6 | 6.0 | 58.0 |
| $X_{180}(T_A R_C) = E_{TA} \cdot E_{RC} \cdot TL(180-)$ | 0.9 | 9.0 | 60.0 |
| $X_{180}(T_A R_C) = E_{TA} \cdot E_{RC} \cdot TL(180+)$ | 1.1 | 11.0 | 58.0 |
| $X_{180}(T_C R_A) = E_{TC} \cdot E_{RA} \cdot TL(180-)$ | 0.9 | 9.0 | 61.5 |
| $X_{180}(T_C R_A) = E_{TC} \cdot E_{RA} \cdot TL(180+)$ | 1.1 | 11.0 | 59.5 |
| $X_{180}(T_B R_D) = E_{TB} \cdot E_{RD} \cdot TL(180-)$ | 0.9 | 9.0 | 60.5 |
| $X_{180}(T_B R_D) = E_{TB} \cdot E_{RD} \cdot TL(180+)$ | 1.1 | 11.0 | 58.5 |
| $X_{180}(T_D R_B) = E_{TD} \cdot E_{RB} \cdot TL(180-)$ | 0.9 | 9.0 | 56.5 |
| $X_{180}(T_D R_B) = E_{TD} \cdot E_{RB} \cdot TL(180+)$ | 1.1 | 11.0 | 54.5 |

In this example, the attenuation for the direct transmission signal has not been determined. Evaluating direct transmission signals in practical systems is often a problem because of electrical interference between the response to the received acoustic signal and the transmitter firing pulse, which occur almost simultaneously in the zero path length examples.

Solving the above equations for the 90° and 180° transmission gives the exemplary sensor efficiencies disclosed below, based on standardising $E_{RA}$ to 30 dB.

| Efficiency | Signal (dB) |
|---|---|
| $E_{RA}$ | 30 |
| $E_{RB}$ | 30.5 |
| $E_{RC}$ | 29 |
| $E_{RD}$ | 28.5 |
| $E_{TA}$ | 40 |
| $E_{TB}$ | 41 |
| $E_{TC}$ | 40.5 |
| $E_{TD}$ | 35 |

These numbers may be used subsequently to find the 16 possible efficiency products of any transmitter/receiver pair. The efficiency products may then be used to calibrate signals produced by the cooperation of any transmitter/receiver pair on a tube under test.

The process above may be carried out at the beginning and end of the run to determine the existence of and measure the magnitude of any changes in the efficiencies. In an ideal situation the electronic components remain stable during an inspection run. However in a practical situation some drift or degeneration may occur. It may be possible to identify sensors where performance degrades by monitoring long term averages of transmission signals (preferably both the direct and 90° signals, if available). The effect of sensor wear may appear the same as a gradual reduction in the performance of the electronics. It may be compensated in a similar fashion.

Sensor lift off and debris may also cause problems. The main mechanisms for sensor lift off are girth welds, seam welds and debris between the sensor and pipe surface. At the girth weld there will be a complete loss of coupling for a certain axial distance and reduced coupling for a short distance either side of this. This reduction will have the appearance of a reduction in the efficiency of the sensors and may be measured in the same way. The seam weld will lift off a sensor, depending on the exact position of the sensor to the weld and the shape of the weld, the effect of this could be a small reduction in the coupling to a complete loss of coupling. It may be assumed that the orientation of the seam weld will be known (detected automatically and checked) so it will be possible to predict which sensors will be affected by the seam weld. The complete lift off of a sensor can be identified by the absence of the transmission signals normally seen by that sensor. If the seam weld has caused only a partial lift off this will be seen as a reduction in the efficiency of the sensor and can be measured and corrected for in the same way, however rather than use long term signal averages it will be necessary to use the transmission signals averaged over a single pipe. The effect of debris will be to lift off a sensor; this could be for a relatively short distance (~1 m) or much longer. This may be seen as a change in the efficiency of the sensor.

To further increase operational reliability, redundancy is provided on the inspection tool by providing additional sensors on each type. To prevent the redundant sensors from increasing background noise (and hence degrading the SNR of the tool mentioned above), they may be housed in a duplicate carrier spaced outside of an interference distance from the primary carrier or carriers. This increase in the quantity of sensors not only compensates for sensors that may be damaged during a pipe inspection, but also provides redundant defect information, which can be used to verify (e.g. provide extra confidence in) the existence, classification, sizing and location of a defect.

Each sensor carrier may include its own drive electronics, signal processing and storage capacity, e.g. contained in the hub.

Figure 6:
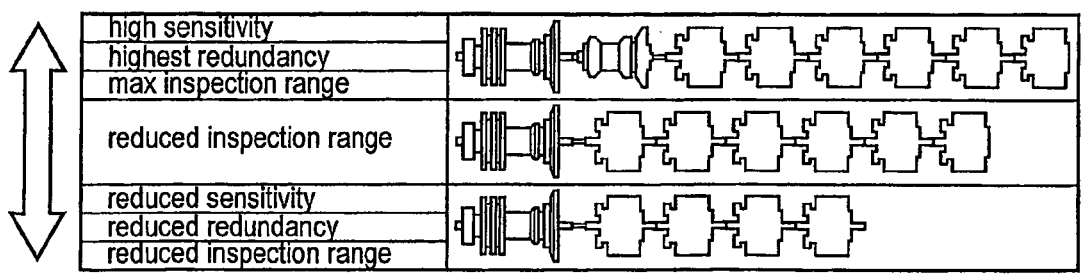
FIG. 6 is a schematic illustration of the modular nature of a pipeline inspection apparatus that is an embodiment of the invention.

FIG. 6 illustrates how the invention may be applied in a modular system. The length of tool (and hence level of sensitivity and redundancy) can be selected according to the requirements of each use situation.

The inspection methods described herein are particularly appropriate for pipeline vehicles required to locate axially oriented cracks. These vehicles normally, irrespective of sensor technology, carry multiple sensors distributed around the circumference of the vehicle. If the sensors are EMATs, they can be directed so that the acoustic propagation direction has the circumferential component necessary to find the cracks. This also allows sensors within the same ring or closely adjacent rings to communicate with each other and obtain the necessary transmission data to correct for attenuation and wall thickness, as discussed above.

If the Lamb/SH calibrated echo ratio is high, the defect is likely to be an inclusion or lamination, if it is low the defect is likely to be a crack or a region of steep sided corrosion. The precise definition of high and low is quantified by a threshold parameter which divides the two cases and is best derived for the system empirically based on a set of know test defects which typically include laminations, inclusions, cracks and corrosion. By this means, EMATs that produce only guided waves and have therefore relatively limited spatial resolution, can provide classification information on a defect which would normally only be possible from a high spatial resolution system. This in turn means that an EMAT sensor system based on guided waves, which is relatively simple and power efficient compared to non-guided wave EMAT systems, becomes feasible in situations where defect classification is essential but power availability is limited and large surface areas of test material must be inspected. The method may be particularly appropriate for a free travelling pipeline inspection vehicle having limited energy storage and required to inspect up to 1 square kilometer of pipe surface in a single mission.

The invention claimed is:

1. A pipeline inspection apparatus comprising:
    a first ultrasound sensor for generating in a pipe wall a first ultrasonic guided wave having a first mode;
    a second ultrasound sensor for generating in the pipe wall a second ultrasonic guided wave having a second mode different from the first mode;
    at least one detector for receiving a first and a second response to the first and second ultrasonic guided waves; and
    a processor in communication with the at least one detector and configured to compare the detected responses to determine a type of defect present in the pipeline.

2. The pipeline inspection apparatus according to claim 1, wherein the at least one detector is arranged to detect the amplitudes of the received responses to the guided waves from both wave modes and the processor is arranged to calculate a ratio of the amplitudes.

3. The pipeline inspection apparatus according to claim 1, wherein the processor is arranged to compare the calculated ratio to a distribution of ratio values for known defects to evaluate the type of defect detected.

4. The pipeline inspection apparatus according to claim 1, wherein the first and second ultrasound sensors are each an electromagnetic acoustic transducer (EMAT).

5. The pipeline inspection apparatus according to claim 4, wherein each sensor is also the at least one detector for echo signals corresponding to its respective wave mode.

6. The pipeline inspection apparatus according claim 1, wherein the sensors are arranged to transmit their guided waves towards a common region.

7. The pipeline inspection apparatus according to claim 1, wherein the first and second wave modes have a main component of particle motion orthogonal to each other.

8. A sensor module mountable on a pipeline vehicle, the sensor module having a plurality of sensors distributed around its periphery, the sensor module comprising:
- a first ultrasound sensor for generating a first ultrasonic guided wave in a pipe wall, the first ultrasonic guided wave having a first mode;
- a second ultrasound sensor for generating a second ultrasonic guided in a pipe wall, the second ultrasonic guided wave having a second mode different from the first mode;
- at least one detector for receiving a first and second response to the first and second ultrasonic guided waves; and
- a processor in communication with the at least one detector and configured to compare the responses to determine a type of defect present in the pipeline.

9. A sensor module according to claim 8, wherein the plurality of sensors comprise a plurality of pairs of SH and SO EMAT sensors arranged to achieve substantially full inspection coverage of the pipeline wall with SH and SO waves as the vehicle travels within a pipeline.

10. A sensor module according to claim 8, wherein the members of each pair of sensors are arranged to be separated from each other around the pipeline vehicle, whereby the members of each pair may lie on opposite sides of a defect in the pipeline wall.

11. A sensor module according to claim 10, wherein a member of each pair of sensors is arranged to detect both a signal from its partner that is transmitted past a defect and its own signal that is reflected by the defect.

* * * * *